US 8,415,641 B2
Apr. 9, 2013

(12) United States Patent
Ono et al.

(10) Patent No.: US 8,415,641 B2
(45) Date of Patent: Apr. 9, 2013

(54) FLUORESCENCE OBSERVATION DEVICE

(75) Inventors: Fumiko Ono, Tokyo (JP); Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/563,259

(22) Filed: Jul. 31, 2012

(65) Prior Publication Data
US 2012/0292530 A1 Nov. 22, 2012

Related U.S. Application Data

(63) Continuation of application No. PCT/JP2011/052315, filed on Feb. 4, 2011.

(30) Foreign Application Priority Data

Feb. 10, 2010 (JP) .................................. 2010-027887

(51) Int. Cl.
G01N 21/64 (2006.01)
(52) U.S. Cl. ................. 250/458.1; 250/461.1; 250/459.1
(58) Field of Classification Search ............... 250/458.1, 250/461.1, 459
See application file for complete search history.

(56) References Cited

U.S. PATENT DOCUMENTS

| 4,768,513 | A | 9/1988 | Suzuki | |
|---|---|---|---|---|
| 6,902,935 | B2 * | 6/2005 | Kaufman et al. | 436/63 |
| 7,102,142 | B2 * | 9/2006 | Sendai | 250/461.1 |
| 7,123,756 | B2 * | 10/2006 | Hakamata et al. | 382/128 |
| 7,361,472 | B2 * | 4/2008 | Yguerabide et al. | 435/7.1 |
| 7,924,432 | B2 * | 4/2011 | Hess et al. | 356/496 |
| 8,055,035 | B2 * | 11/2011 | Okugawa et al. | 382/128 |
| 2002/0168096 | A1 * | 11/2002 | Hakamata et al. | 382/132 |
| 2002/0197728 | A1 * | 12/2002 | Kaufman et al. | 436/164 |

(Continued)

FOREIGN PATENT DOCUMENTS

| JP | 62-247232 A | 10/1987 |
|---|---|---|
| JP | 2000-325294 A | 11/2000 |
| JP | 2003-36436 A | 2/2003 |
| JP | 2004-24497 A | 1/2004 |

OTHER PUBLICATIONS

International Search Report dated Mar. 8, 2011 issued in PCT/JP2011/052315.
International Search Report PCT/JP2011/0532315 dated Mar. 8, 2011 together with an English language translation.

*Primary Examiner* — David Porta
*Assistant Examiner* — Djura Malevic
(74) *Attorney, Agent, or Firm* — Scully Scott Murphy & Presser, PC

(57) ABSTRACT

In a fluorescence observation device, a light source device generates illumination light and excitation light to be radiated onto an examination subject; a white-light image data acquisition unit generates a white-light image by capturing reflected light coming from the examination subject; a fluorescence image data acquisition unit generates a fluorescence image by capturing fluorescence generated at the examination subject; a quantification computation unit computes normalized fluorescence intensities, which are brightness values of individual pixels in the fluorescence image normalized by brightness values of corresponding pixels in the white-light image; a standard-data memory stores standard data indicating a typical correspondence relationship between the normalized fluorescence intensities and states of the examination subject; and an image-correction computation unit judges the states of the examination subject that correspond to the individual normalized fluorescence intensities on the basis of a minimum value of the normalized fluorescence intensities and the standard data.

5 Claims, 13 Drawing Sheets

U.S. PATENT DOCUMENTS

2003/0207250 A1* 11/2003 Kaufman et al. .................. 435/4
2003/0218137 A1* 11/2003 Sendai ....................... 250/461.1
2005/0064602 A1* 3/2005 Kaufman et al. ............. 436/164
2009/0080722 A1* 3/2009 Okugawa et al. ............. 382/128

* cited by examiner

| LESION LEVEL | 1 | 2 | 3 | 4 | 5 |
|---|---|---|---|---|---|
| STANDARD DATA 1 | 0~5 | 5~10 | 10~15 | 15~20 | 20~25 |
| STANDARD DATA 2 | 6~10 | 10~14 | ... | | |
| STANDARD DATA 3 | . | | | | |
| STANDARD DATA 4 | . | | | | |
| STANDARD DATA 5 | | | | | |

FLUORESCENCE OBSERVATION DEVICE

TECHNICAL FIELD

The present invention relates to a fluorescence observation device.

BACKGROUND ART

In the related art, there is a known fluorescence observation device (for example, see Patent Literature 1) which is employed in, for example, an endoscope device and with which a lesion area is diagnosed by using a fluorescent agent.

CITATION LIST

Patent Literature

{PTL 1} Japanese Unexamined Patent Application, Publication No. Sho 62-247232

SUMMARY OF INVENTION

Solution to Problem

The present invention employs a fluorescence observation device including an illumination light source that generates illumination light and excitation light to be radiated onto an examination subject; a return-light image generating unit that generates a return-light image by capturing return light coming from the examination subject due to the illumination light emitted from the illumination light source; a fluorescence image generating unit that generates a fluorescence image by capturing fluorescence generated at the examination subject due to the excitation light emitted from the illumination light source; a normalization computation unit that computes normalized fluorescence intensities, which are brightness values of individual pixels in the fluorescence image generated by the fluorescence image generating unit normalized by brightness values of corresponding pixels in the return light image; a standard-data storage unit that stores standard data that indicate a typical correspondence relationship between the normalized fluorescence intensities and states of the examination subject; and a state judging unit that judges the states of the examination subject that correspond to the individual normalized fluorescence intensities on the basis of a minimum value of the normalized fluorescence intensities computed by the normalization computation unit and the standard data stored in the standard-data storage unit.

In the above-described invention, the state judging unit may calculate the difference between a minimum value of the normalized fluorescence intensities in the same image computed by the normalization computation unit and a minimum value of the standard data, and may judge, by using the standard data, states of the examination subject which correspond to the corrected fluorescence intensities obtained by adding the calculated difference to the individual normalized fluorescence intensities.

The above-described invention may be provided with a minimum-value storage unit that stores a minimum value of the normalized fluorescence intensities in the same image computed by the normalization computation unit; and a minimum-value updating unit that updates the minimum value stored in the minimum-value storage unit in the case in which a minimum value of the normalized fluorescence intensities in a newly acquired image for the same imaging target is smaller than the minimum value stored in the minimum-value storage unit.

In the above-described invention, the standard-data storage unit may store multiple sets of standard data having different minimum values; and the state judging unit may select the standard data having a minimum value closest to the minimum value of the normalized fluorescence intensities in the same image, which are computed by the normalization computation unit, and may judge, by using the selected standard data, states of the examination subject which correspond to the individual normalized fluorescence intensities.

In the above-described invention, the state judging unit may interpolate states of the examination subject from the minimum value to the maximum value of the standard data stored in the standard-data storage unit with a predetermined function to be associated with the individual normalized fluorescence intensities between the minimum value of the normalized fluorescence intensities in the same image calculated by the normalization computation unit and the maximum value of the normalized fluorescence intensities in the standard data.

DESCRIPTION OF EMBODIMENTS

First Embodiment

A fluorescence observation device 1 according to a first embodiment of the present invention will be described below with reference to the drawings. Here, an example in which the fluorescence observation device 1 according to this embodiment is applied to an endoscope device will be described.

As background for employing the present invention, the following is assumed: Generally in endoscope observation employing a fluorescence observation device, generally there is a correlative relationship between the lesion level and the gradation value of fluorescence intensities in an observation area, and the gradation value increases with an increase in the lesion level. Although this correlative relationship is found in all examinees, the rates of change show individual variation. Therefore, if an observation is performed without removing the influence of this individual variation, quantitative diagnosis becomes difficult, which gives decreased diagnosis precision.

Figure 1:
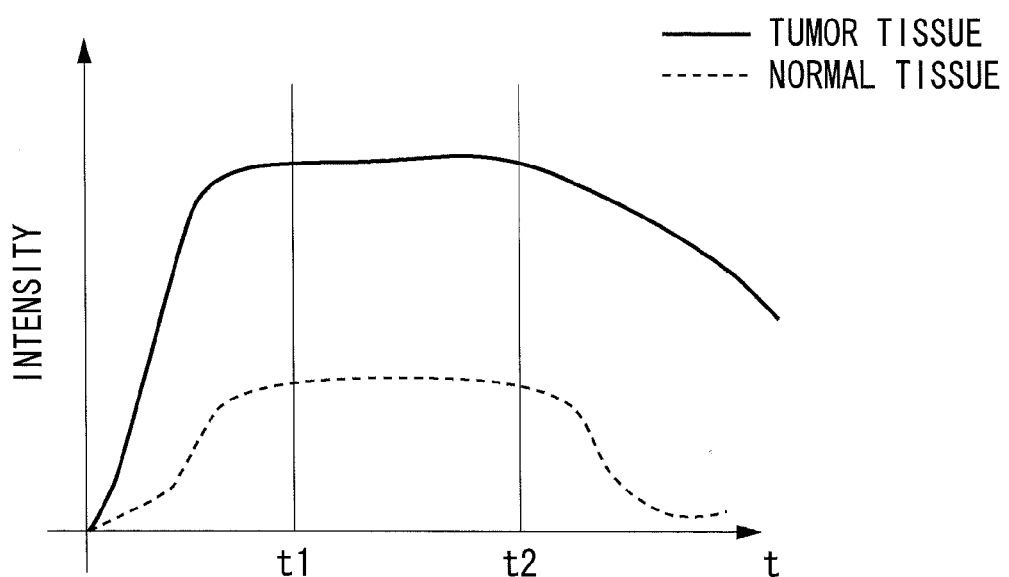
FIG. 1 illustrates a graph showing time dependency in the process of uptake and seepage of fluorescent dye in normal tissue and tumor tissue.

FIG. 1 shows time dependency in the process of uptake and seepage of fluorescent dye in normal tissue and tumor tissue.

Observation conditions under which the present invention is applied include the following conditions. As shown in FIG. 1, in the process in which an agent (fluorescent dye) is taken up by and seeps out from a biological specimen, the normal tissue and the tumor tissue differ in terms of the time dependency in absorption and release of the agent. The observation conditions for the present invention are that observation is performed under condition of $t1<t<t2$, that is, the observation is performed during a period in which the temporal change in dye uptake is stable both in the normal tissue and the tumor tissue.

Figure 2:
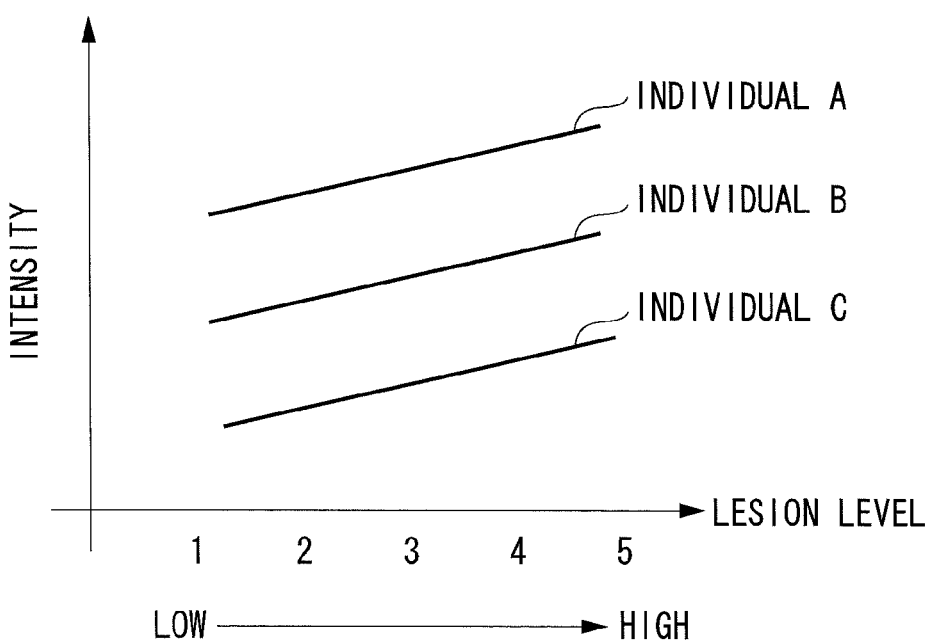
FIG. 2 illustrates a graph showing the correlative relationship between the lesion level and the gradation value.

Further, as shown in FIG. 2, with regard to the correlation between the lesion level and the gradation value, the correlative relationship between lesion levels (lesion levels 1 to 5) and associated gradation values is assumed to maintain linearity. Although there is individual variation in the ranges of the gradation values for the normal tissue and the tumor tissue, it is assumed that the slopes thereof are constant, and thus, they are in a parallel relationship for all individuals.

The configuration of the fluorescence observation device 1 according to this embodiment will be described below.

Figure 3:
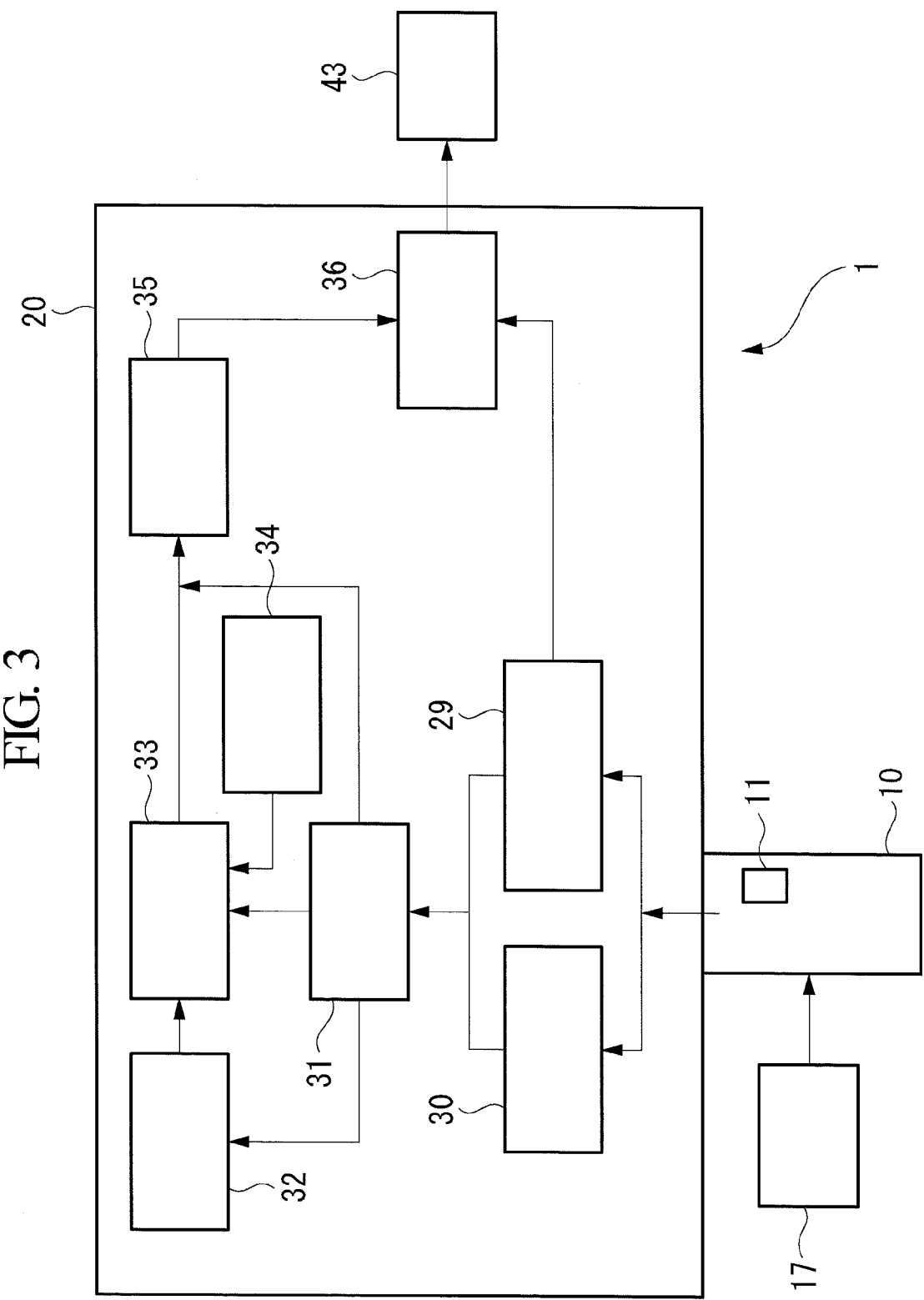
FIG. 3 is a functional block diagram of a fluorescence observation device according to a first embodiment of the present invention.

As shown in FIG. 3, the fluorescence observation device 1 according to this embodiment is provided with a scope 10 that is inserted into a body cavity, a light source device (illumination light source) 17 that generates light, an image computation unit 20 that computes an image acquired by the scope 10, and a monitor 43 that displays an image computed by the image computation unit 20.

The scope 10 has a long, thin shape and a light guide fiber (not shown) is provided in the interior thereof. One end of the light guide fiber extends to a distal end of the scope 10 and the other end thereof is connected to the light source device 17. By doing so, light emitted from the light source device 17 is guided to the distal end of the scope 10 to be radiated into the body cavity.

The scope 10 is provided with an image-display changing switch 11 that changes images to be displayed on the monitor 43.

The scope 10 and the image computation unit 20 are connected with an image transmission cable (not shown). The image computation unit 20 and the monitor 43 are connected with a monitor cable (not shown). Accordingly, image data acquired by the scope 10 are sent to the image computation unit 20 by being transmitted through the image transmission cable. The image computation unit 20 applies image processing to the image data sent thereto, which are subsequently transmitted to the monitor 43 through the monitor cable to be displayed on a monitor screen.

The light source device 17 is, for example, a xenon lamp, and generates white light (illumination light) and excitation light. Light generated from the xenon lamp passes through a wavelength selection filter (not shown), thereby allowing white light and excitation light in set wavelength bands to be transmitted.

The white light and the excitation light emitted from the light source device 17 are guided through the light guide fiber in the scope 10 to be radiated onto an examination subject from the distal end of the scope 10. By irradiating the examination subject with the white light, reflected light coming from the examination subject enters an imaging optical system (not shown) disposed at the distal end of the scope 10. By irradiating the examination subject with the excitation light, fluorescence is generated at the examination subject, and the fluorescence enters the imaging optical system.

The fluorescence and the reflected light entering the imaging optical system are split by a splitter (not shown) and are detected by CCDs (not shown) that detect the respective types of light. The reflected light coming from the examination subject detected by the white-light CCD is sent to a white-light image data acquisition unit (return-light image generating unit) 29 in the image computation unit 20 via the image transmission cable. On the other hand, the fluorescence detected by the fluorescence CCD is sent to a fluorescence image data acquisition unit (fluorescence image generating unit) 30 in the image computation unit 20 via the image transmission cable.

As its functions, the image computation unit 20 is provided with the white-light image data acquisition unit 29, the fluorescence image data acquisition unit 30, a quantification computation unit (normalization computation unit) 31, a minimum-value acquisition unit (minimum-value storage unit) 32, a correction-value determining unit (minimum-value updating unit) 33, a standard-data memory (standard-data storage unit) 34, an image-correction computation unit 35, and an image combining unit (state judging unit) 36.

The white-light image acquisition unit 29 generates a white-light image from the white-light image data detected by the white-light CCD. The white-light image acquisition unit 29 sends the generated white-light image to the quantification computation unit 31 and the image combining unit 36.

The fluorescence image data acquisition unit 30 generates a fluorescence image from the fluorescence image data detected by the fluorescence CCD. The fluorescence image data acquisition unit 30 sends the generated fluorescence image to the quantification computation unit 31.

The quantification computation unit 31 computes normalized fluorescence intensities by normalizing brightness values of individual pixels in the fluorescence image by brightness values of individual pixels in the white-light image. Specifically, the quantification computation unit 31 divides the brightness values of the individual pixels in the fluorescence image generated by the fluorescence image data acquisition unit 30 by the brightness values of the individual pixels, corresponding to the individual pixels in the fluorescence image, in the white-light image generated by the white-light image data acquisition unit 29, thereby computing the normalized fluorescence intensities for which the brightness values of the individual pixels are normalized. The quantification computation unit 31 sends the computed normalized fluorescence intensities to the minimum-value acquisition unit 32, the correction-value determining unit 33, and the image-correction computation unit 35.

Figure 4:
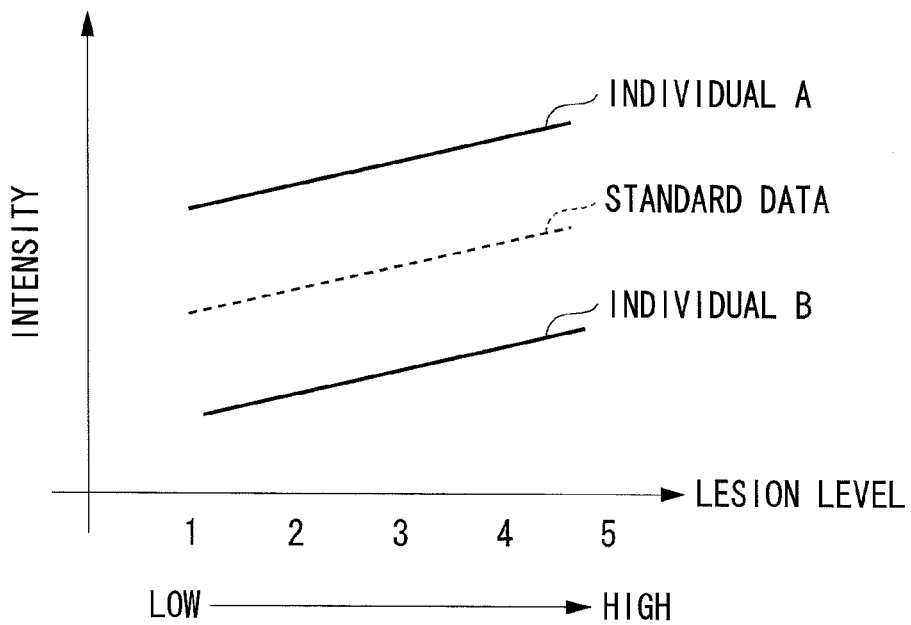
FIG. 4 illustrates a graph of standard data indicating a typical correlative relationship between the lesion level and the gradation value.

The standard-data memory 34 stores standard data that indicate a typical correspondence relationship between normalized fluorescence intensities and states of an examination subject. As shown in FIG. 4, the standard data are average values obtained as a result of examining the association between the lesion levels and the gradation values for numerous examinees. The storage method thereof is assumed to be storage in the form of an equation or a table. Note that the standard data are the normalized fluorescence intensity data obtained by normalizing (dividing) the fluorescence image by the white-light image in order to reduce the influence on the image data due to the influences of the distance and angle between the distal end of the scope 10 and an observation area.

Figure 5:
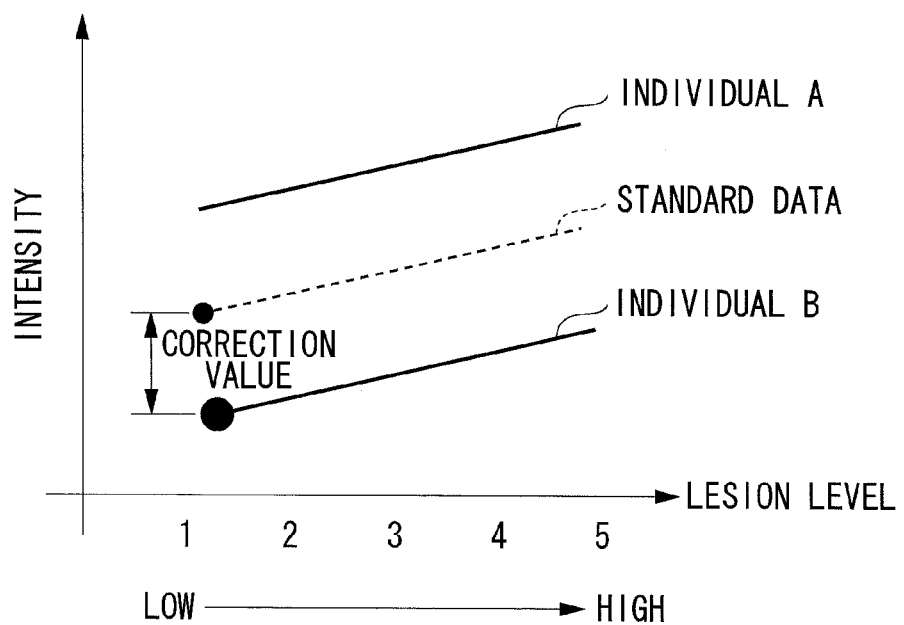
FIG. 5 illustrates a graph showing a method of determining a correction value.

The minimum-value acquisition unit 32 acquires a minimum value of the normalized fluorescence intensities (gradation values) in the same image from the normalized fluorescence intensities for the individual pixels computed by the quantification computation unit 31 and stores this minimum value. As shown in FIG. 5, the minimum-value acquisition unit 32 sets the acquired minimum value to be a lesion level 1.

The correction-value determining unit 33 determines a correction value for correcting the normalized fluorescence intensities by using the normalized fluorescence intensities computed by the quantification computation unit 31 and the standard data stored in the standard-data memory 34. Specifically, as shown in FIG. 5, the correction-value determining unit 33 calculates the difference between the minimum value of the normalized fluorescence intensities in the same image computed by the quantification computation unit 31 and the minimum value of the standard data stored in the standard-data memory 34 and determines the difference to be the correction value.

Further, in the case in which a minimum value of normalized fluorescence intensities for a newly acquired image of the same imaging target is smaller than the minimum value stored in the minimum-value acquisition unit 32, the correction-value determining unit 33 updates the minimum value stored in the minimum-value acquisition unit 32, and determines the updated minimum value to be a new correction value. This updating is performed at any time as needed during observation.

Figure 6:
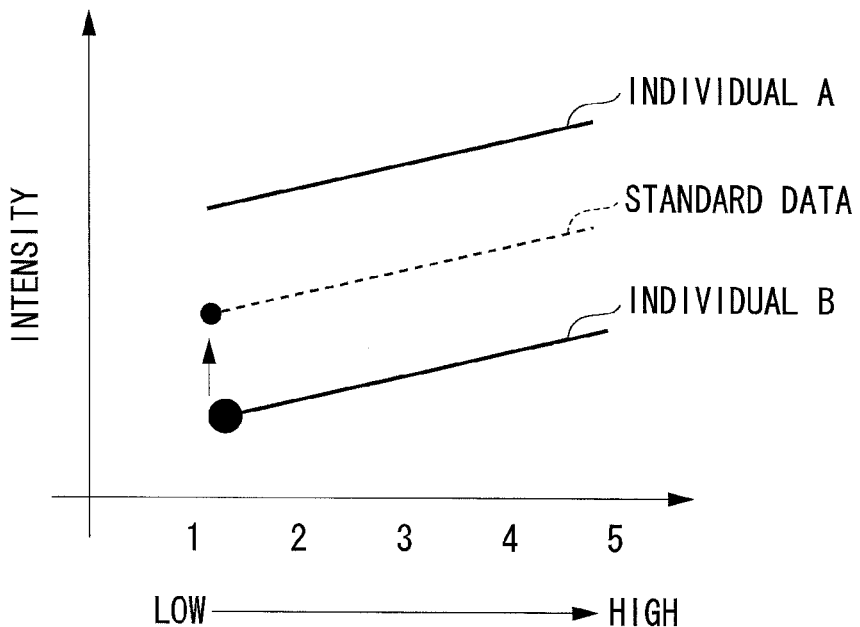
FIG. 6 illustrates a graph showing a method of correcting normalized fluorescence intensities.

The image-correction computation unit 35 corrects the normalized fluorescence intensities computed by the quantification computation unit 31 by using the correction value determined by the correction-value determining unit 33. Specifically, as shown in FIG. 6, the image-correction computation unit 35 corrects normalized fluorescence intensities for an individual B so as to have the same intensities as the standard data by, for example, adding to (or subtracting from) the normalized fluorescence intensities for the individual B the correction value which is the difference between a minimum value of the normalized fluorescence intensities for the individual B and the minimum value of the standard data.

Figure 7:
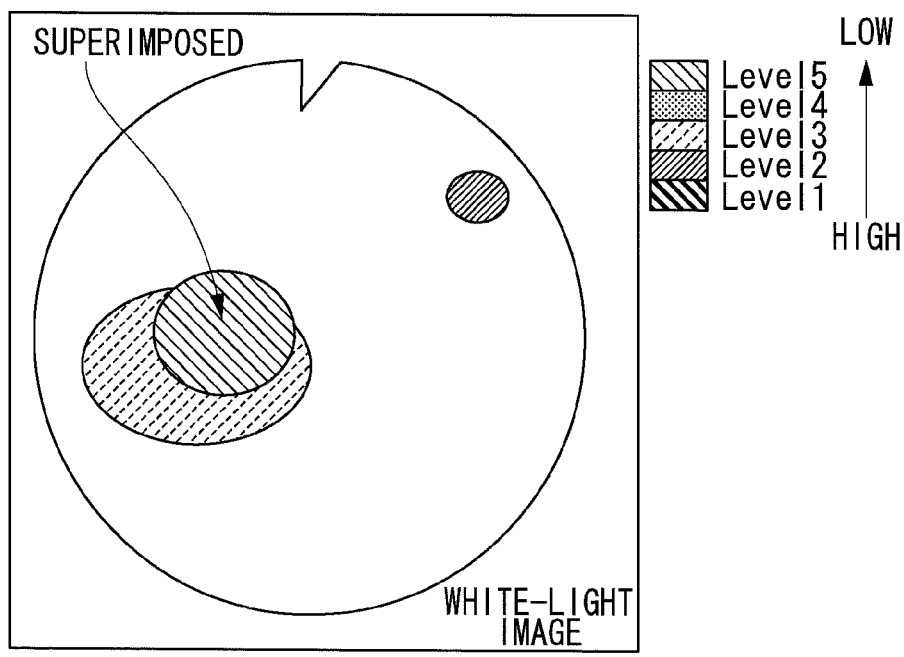
FIG. 7 is a diagram showing an example screen in which the lesion levels are separately displayed.

The image combining unit 36 generates a combined image by combining the white-light image generated by the white-light image data acquisition unit 29 and the normalized fluorescence intensities corrected by the image-correction computation unit 35. Specifically, as shown in FIG. 7, the image combining unit 36 classifies the normalized fluorescence intensities normalized by the image-correction computation unit 35 into levels 1 to 5 of the lesion levels in accordance with the gradation values. Furthermore, the image combining unit 36 displays, for example, areas of level 3 or above in color, superimposes them on the white-light image data, and thus, displays lesion sites.

The image-display changing switch 11 allows a user to set with which observation mode among a plurality of observation modes an image is displayed on the monitor 43. Here, the plurality of observation modes are, for example, an observation mode in which the white-light image generated by the white-light image data acquisition unit 29 is displayed on the monitor 43 without modification (white-light-image observation mode), an observation mode in which the combined image generated by the image combining unit 36 is displayed on the monitor 43 (combined-image observation mode), and an observation mode in which the white-light image and the combined image are simultaneously displayed (dual-image observation mode).

The monitor 43 displays the image selected by the image-display changing switch 11.

That is, the white light and the excitation light coming from the light source device are radiated onto the examination subject, the white-light image generating unit generates the white-light image from the reflected light of the white light, and the fluorescence image data acquisition unit also generates the fluorescence image from the fluorescence generated by radiating the excitation light onto the examination subject. Then, the quantification computation unit computes the normalized fluorescence intensities, which are the brightness values of the individual pixels in the fluorescence image normalized by the brightness values of corresponding pixels in the white-light image. Based on the minimum value of the normalized fluorescence intensities computed in this way and the standard data stored in the standard-data memory, the image combining unit judges the states of the examination subject that correspond to the individual normalized fluorescence intensities.

Figure 8:
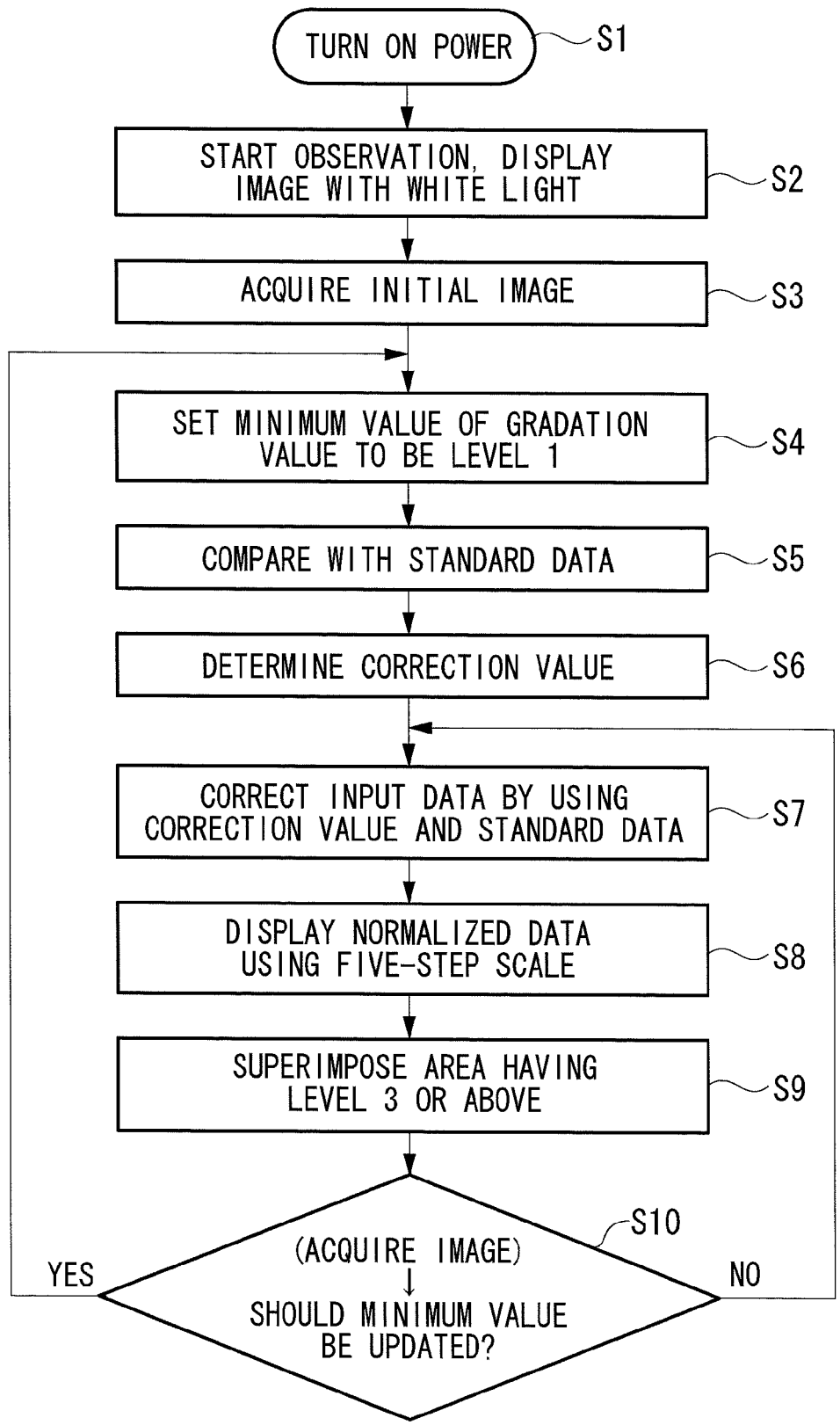
FIG. 8 is a flowchart showing the processing executed by the fluorescence observation device in FIG. 3.

The operation of the fluorescence observation device 1 having the above-described configuration will be described below by using a flowchart shown in FIG. 8.

First, the fluorescence observation device 1 of this embodiment is turned on (Step S1).

Next, once observation of an examination subject is started by inserting the scope 10 into the body cavity, light coming from the light source device 17 is radiated onto the examination subject via the light guide fiber in the scope 10. By doing so, the white-light image data acquisition unit 29 acquires a white-light image generated from the reflected light coming from the examination subject, and the fluorescence image data acquisition unit 30 acquires a fluorescence image generated from the fluorescence emitted from the examination subject (Step S2).

Next, an initial image is acquired from an area assumed to be normal tissue (Step S3). At this time, by dividing the brightness values of the fluorescence image by the brightness values of the white-light image for the individual pixels by means of the quantification computation unit 31, the normalized fluorescence intensities for which the brightness values of the individual pixels have been normalized are computed.

Next, as shown in FIG. 5, the minimum value is acquired from the normalized fluorescence intensities for the individual pixels, excluding abnormal values, and the acquired minimum value of the normalized fluorescence intensities is set to be the lesion level 1 (Step S4).

Next, the minimum value of the normalized fluorescence intensities for the same image computed by the quantification computation unit 31 and the minimum value of the standard data stored in the standard-data memory 34 are compared (Step S5), and the difference between these minimum values is determined to be the correction value (Step S6).

Next, as shown in FIG. 6, by using the correction value determined in this way, the normalized fluorescence intensities computed by the quantification computation unit 31 are corrected (Step S7).

Next, the normalized fluorescence intensities normalized by the image-correction computation unit 35 are classified into levels 1 to 5, that is, a five-step scale of lesion levels, in accordance with the gradation values, and the normalized fluorescence intensities are displayed using the five-step scale (Step S8).

Next, as shown in FIG. 7, for example, areas at or above level 3 are displayed in color, and, by superimposing them on the white-light image data, the lesion sites are displayed (Step S9). Note that the color display may be used for levels other than three.

During the observation, the minimum value of the gradation values is obtained in real time from the image data acquired in the process of inserting the endoscope into the body to update the minimum value of the normalized fluorescence intensities (Step S10). When a normalized fluorescence intensity smaller than an initially-set value is acquired, the process returns to Step S4 to reset the minimum value, and the correction value is changed using this value to correct the normalized fluorescence intensities.

As described above, with the fluorescence observation device 1 according to this embodiment, the influences of the observation distance and observation angle on the fluorescence intensity can be eliminated by judging the state of the examination subject on the basis of the normalized fluorescence intensities normalized by the white-light image, which makes it possible to enhance observation precision for the lesion area.

Further, because the states of the examination subject are judged on the basis of the minimum value of the normalized fluorescence intensities computed by the quantification computation unit 31 and the standard data which indicate the typical correspondence relationship between the normalized fluorescence intensities and the state of the examination subject, it is possible to eliminate, as much as possible, the influence of individual variation on the fluorescence intensities. Accordingly, it is possible to perform quantitative observation regardless of the individual variation, which makes it possible to perform high-precision observation even with different patients.

Furthermore, by adding the difference between the minimum value of the normalized fluorescence intensities and the minimum value of the standard data to the individual normalized fluorescence intensities, it is possible to easily generate the corrected fluorescence intensities, which serve as references for judging the states of the examination subject. Accordingly, the states of the examination subject can be judged by eliminating the influence of the individual variation by means of simple computations, which makes it possible to perform the processing for judging the states of the examination subject at high speed.

Moreover, in the case in which the minimum value of the normalized fluorescence intensities is smaller than the minimum value stored in the minimum-value acquisition unit 32, the correction value can be reset as needed by updating the minimum value stored in the minimum-value acquisition unit 32, which makes it possible to change the corrected fluorescence intensities which serve as the references for judging the states of the examination subject in real time. Accordingly, the states of the examination subject can be judged more accurately, which makes it possible to enhance the observation precision for the lesion area.

Figure 9:
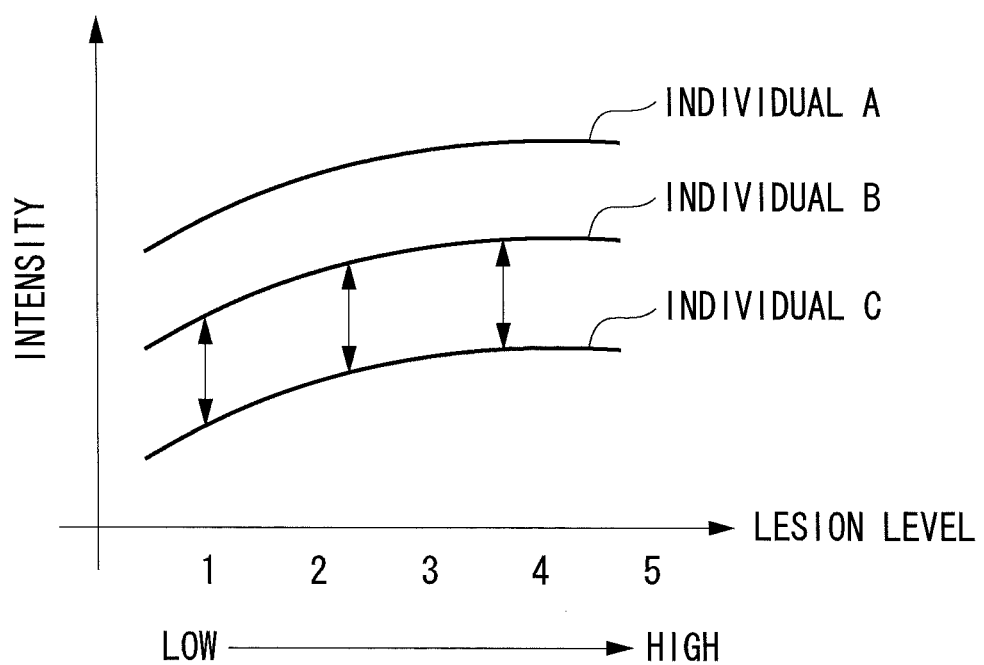
FIG. 9 illustrates a graph showing the correlative relationship between the lesion level and the gradation value.

Note that, even in the case in which the correlation between the lesion levels and the gradation values takes the form of a curve instead of being linear, as shown in FIG. 9, the fluorescence observation device 1 according to this embodiment can be applied so long as the differences among individuals are constant.

Second Embodiment

Next, a fluorescence observation device 2 according to a second embodiment of the present invention will be described with reference to the drawings. In describing this embodiment, descriptions of commonalities with the fluorescence observation device 1 according to the first embodiment will be omitted, and differences will mainly be described.

The fluorescence observation device 2 according to this embodiment differs from the fluorescence observation device 1 according to the first embodiment in that multiple sets of standard data are stored in the standard-data memory 34.

Figure 10:
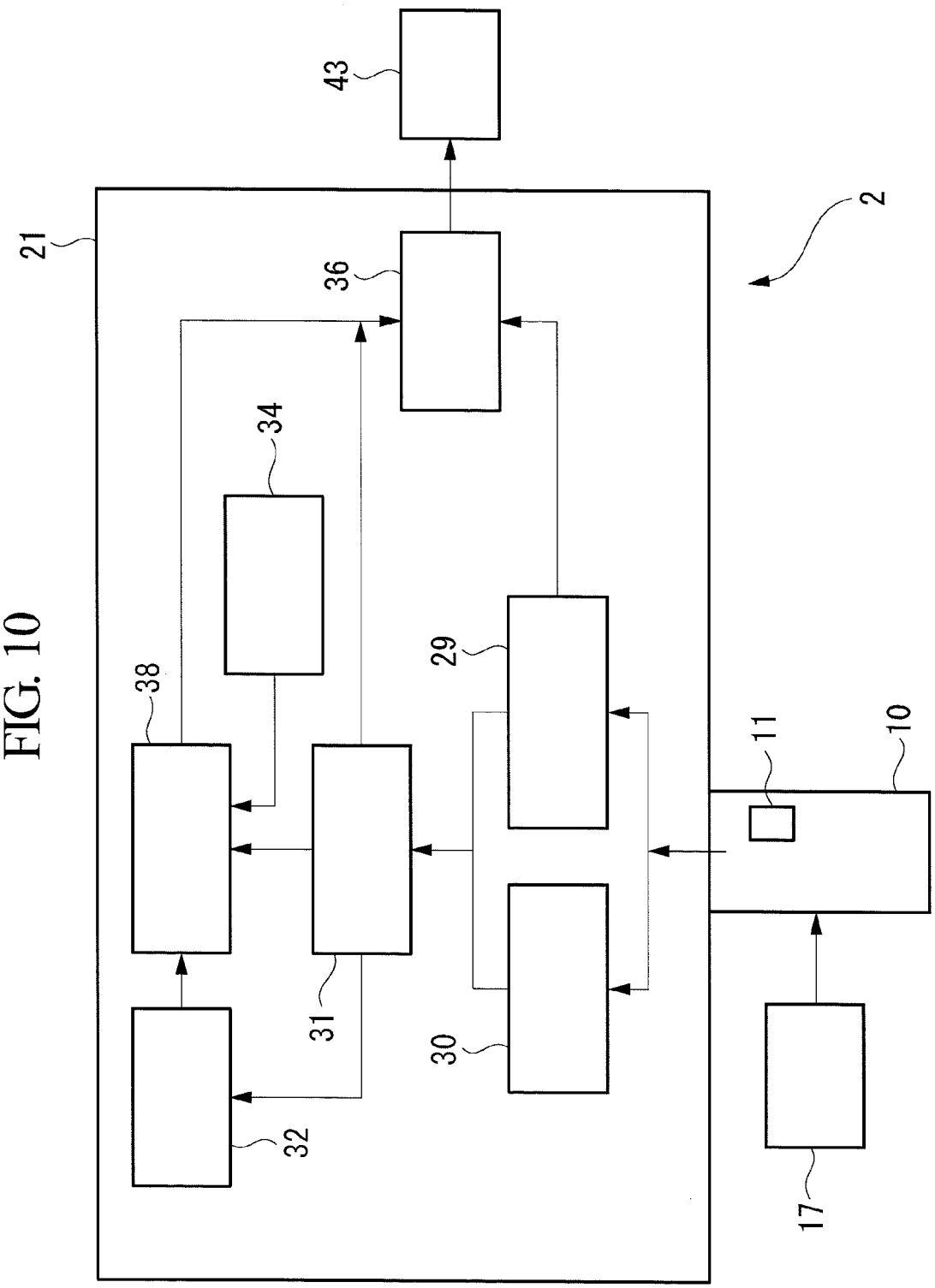
FIG. 10 is a functional block diagram of a fluorescence observation device according to a second embodiment of the present invention.

As shown in FIG. 10, in the fluorescence observation device 2 according to this embodiment, the image computation unit 21 is provided with, as its functions, the white-light image data acquisition unit 29, the fluorescence image data acquisition unit 30, a quantification computation unit (normalization computation unit) 31, the minimum-value acquisition unit (minimum-value storage unit) 32, an appropriate-standard-data determining unit 38, the standard-data memory (standard-data storage unit) 34, and the image combining unit (state judging unit) 36.

Figures 11, 12:
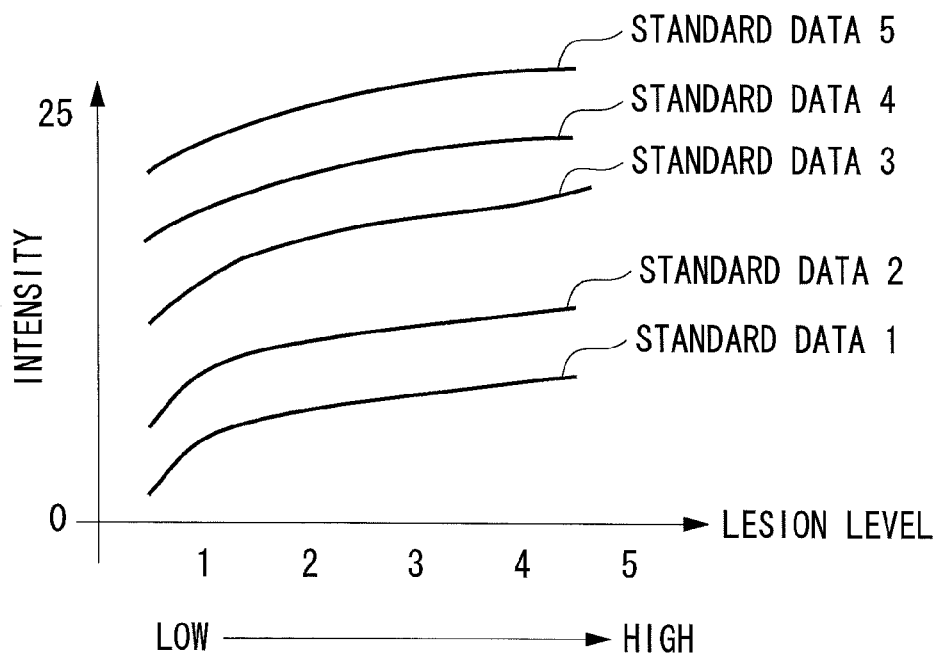
FIG. 11 illustrates a graph of multiple sets of standard data stored in a standard-data memory in FIG. 10.
FIG. 12 is a table showing the correlative relationship between the lesion level and the gradation value for the multiple sets of standard data in FIG. 11.

As shown in FIG. 11, the multiple sets of standard data having different minimum values are stored in the standard data memory 34. These standard data are the results of examining the association between the lesion levels and the gradation values for a plurality of examinees. As shown in FIG. 12, the gradation values in these standard data are sectioned according to the lesion levels, and are stored in the form of a table in the standard-data memory 34. Note that, although the correlation between the lesion levels and the gradation values does not necessarily need to be linear, it is assumed to be a positive correlation.

From the multiple sets of standard data stored in the standard-data memory 34, the appropriate-standard-data determining unit 38 selects the standard data having a minimum value closest to the minimum value of the normalized fluorescence intensities in the same image computed by the quantification computation unit 31.

Figure 13:
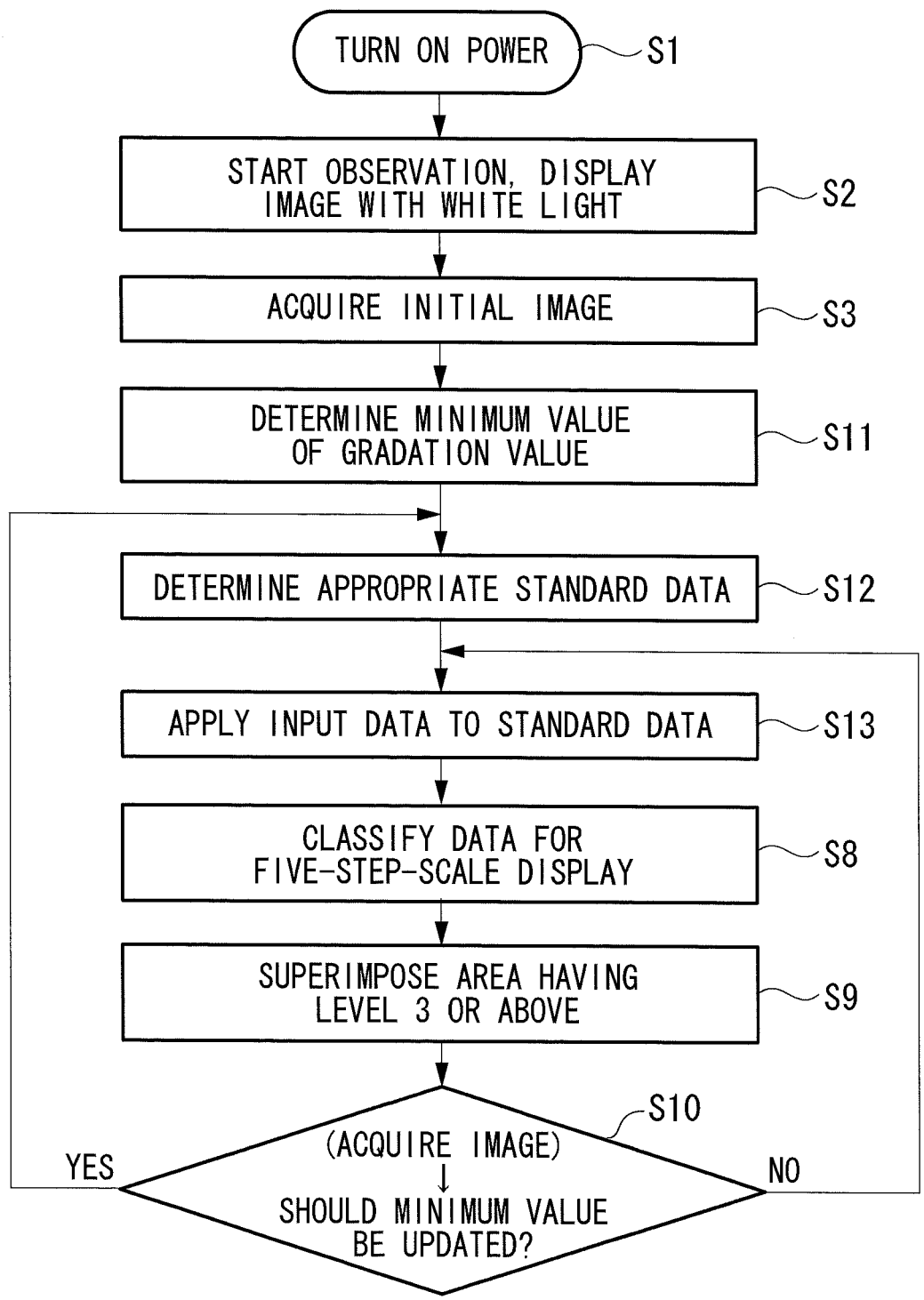
FIG. 13 is a flowchart showing the processing executed by the fluorescence observation device in FIG. 10.

The operation of the fluorescence observation device 2 having the above-described configuration will be described below by using a flowchart shown in FIG. 13.

First, the fluorescence observation device 2 of this embodiment is turned on (Step S1).

Next, once observation of an examination subject is started by inserting the scope 10 into the body cavity, light coming from the light source device 17 is radiated onto the examination subject via the light guide fiber in the scope 10. By doing so, the white-light image data acquisition unit 29 acquires a white-light image generated from the reflected light coming from the examination subject, and the fluorescence image data acquisition unit 30 acquires a fluorescence image generated from the fluorescence emitted from the examination subject (Step S2).

Next, an initial image is acquired from an area assumed to be normal tissue (Step S3). At this time, by dividing the brightness values of the fluorescence image by the brightness values of the white-light image for the individual pixels by means of the quantification computation unit 31, the normalized fluorescence intensities for which the brightness values of the individual pixels have been normalized are computed.

Next, the minimum-value acquisition unit 32 determines the minimum value of the normalized fluorescence intensities for the individual pixels, excluding abnormal values (Step S11).

Then, the appropriate-standard-data determining unit 38 selects from the multiple sets of standard data stored in the standard-data memory 34 the standard data having a minimum value closest to the minimum value determined in Step S11 (Step S12).

Next, the normalized fluorescence intensities are corrected by applying the normalized fluorescence intensities computed by the quantification computation unit 31 to the selected standard data (Step S13).

Next, the normalized fluorescence intensities normalized by the image-correction computation unit 35 are classified into levels 1 to 5, that is, the five-step scale of lesion levels, in accordance with the gradation values, and the normalized fluorescence intensities are displayed in the five-step scale (Step S8).

Next, for example, areas at or above level 3 are displayed in color, and, by superimposing them on the white-light image data, the lesion sites are displayed (Step S9). Note that the color display may be used for levels other than level 3.

During the observation, the minimum value of the gradation values is obtained in real time from the image data acquired in the process of inserting the endoscope into the body to update the minimum value of the normalized fluorescence intensities (Step S10). When a normalized fluorescence intensity smaller than an initially-set value is acquired, the process returns to Step S12 to reselect the standard data, and the normalized fluorescence intensities are corrected on the basis of the selected new standard data.

As described above, with the fluorescence observation device 2 according to this embodiment, by using the standard data having the minimum value closest to the minimum value of the normalized fluorescence intensities, it is possible to correct the normalized fluorescence intensities such that various patterns of individual variation can be handled in detail. Accordingly, the standard data can be properly used in accordance with patients or observation areas, which makes it possible to enhance observation precision for the lesion area.

That is, by judging the states of the examination subject corresponding to the individual normalized fluorescence intensities by using the standard data having the minimum value closest to the minimum value of the normalized fluorescence intensities, it is possible to properly use the standard data in accordance with patients or observation areas, which makes it possible to enhance observation precision for the lesion area.

Further, because the normalization to the standard data is performed by associating the minimum value of the normalized fluorescence intensities with the standard data stored in the standard-data memory 34, without involving the image-correction computation unit 35 (see FIG. 3), the amount of computation can be reduced. Accordingly, the processing speed for the image data can be enhanced, and the observation image can be smoothly displayed on the monitor 43.

Note that the fluorescence observation device 2 according to this embodiment is also applicable in the case in which the correlation between the lesion levels and the gradation values is complicated or the case in which graphs of the standard data for respective individuals, that is, graphs showing the correspondence relationships between the normalized fluorescence intensities and the lesion levels for the respective individuals, are not in a parallel relationship.

Third Embodiment

Next, a fluorescence observation device 3 according to a third embodiment of the present invention will be described with reference to the drawings. In describing this embodiment, descriptions of commonalities with the fluorescence observation devices 1 and 2 according to each of the embodiments described above will be omitted, and differences will mainly be described.

The fluorescence observation device 3 according to this embodiment differs from the fluorescence observation devices 1 and 2 according to each of the embodiments described above in that correlative relationships between the lesion level and the gradation value differ depending on the individuals.

Observation conditions under which the fluorescence observation device 3 according to this embodiment is employed include the following conditions. As with each of the embodiments described above, the observation is performed during a period in which temporal change in dye uptake is stable both in the normal tissue and the tumor tissue. The correlative relationships between the lesion level and the gradation value are assumed to be positive correlations and to be linear.

Figure 15:
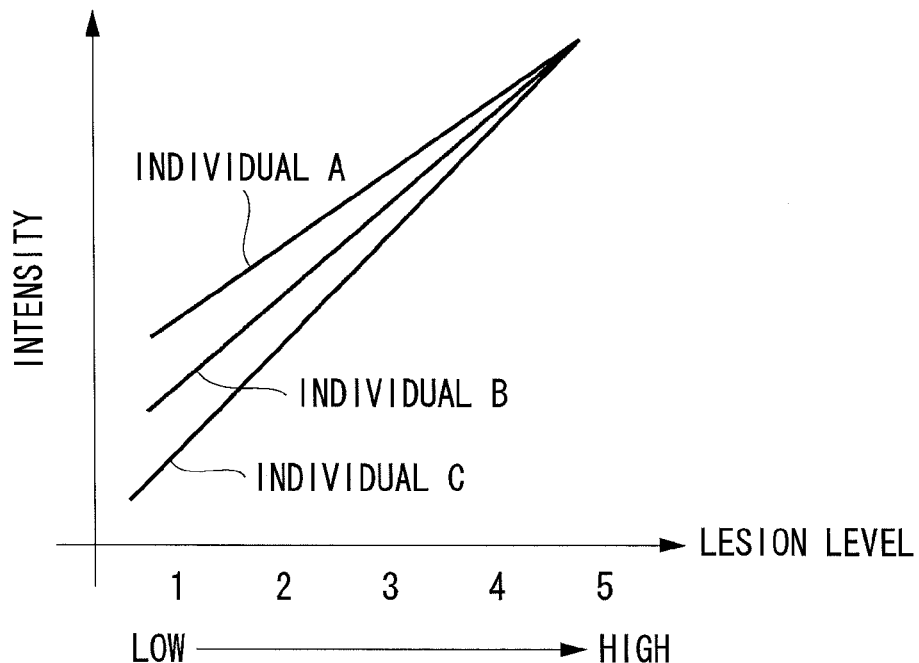
FIG. 15 illustrates a graph showing the correlative relationship between the lesion level and the gradation value.

As shown in FIG. 15, the observation conditions for this embodiment differ from the observation conditions for each of the embodiments described above in that the gradation values of tumor portions having large gradation values are affected little by the individual variation; however, the influence of the individual variation increases with an increase in proximity to the normal tissue, that is, with a decrease in the lesion level.

Figure 16:
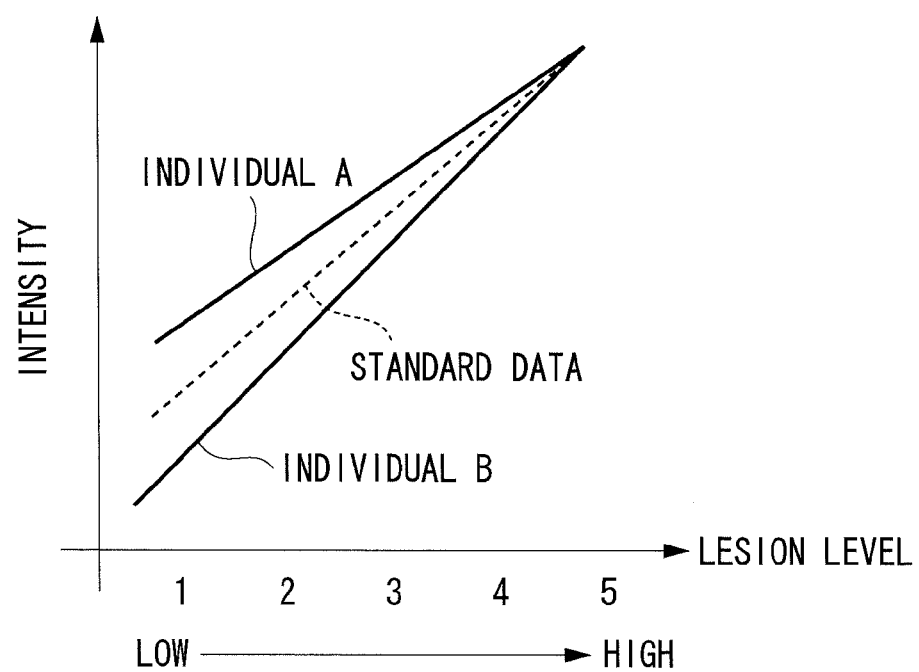
FIG. 16 illustrates a graph of standard data showing a typical correlative relationship between the lesion level and the gradation value.
Figure 17:
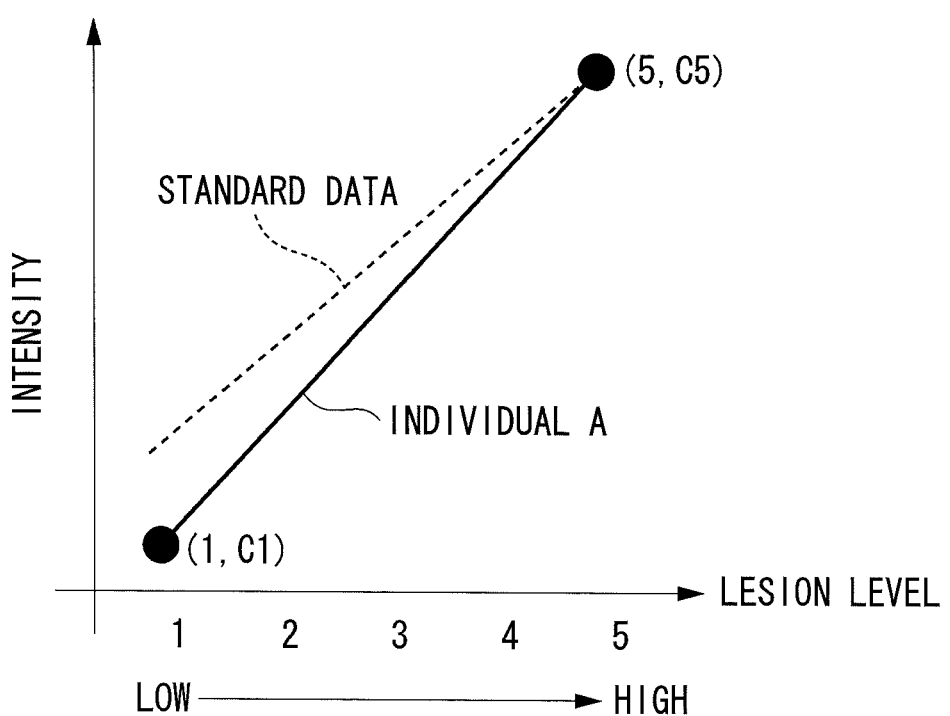
FIG. 17 illustrates a graph showing a method of correcting normalized fluorescence intensities.

As shown in FIG. 16, the standard data stored in the standard-data memory 34 are, as with the first embodiment, average values obtained as a result of examining the association between the lesion levels and the gradation values for numerous examinees. As shown in FIG. 17, in the fluorescence observation device 3 according to this embodiment, the individual variation is corrected by using the gradation value of the maximum lesion level in the standard data stored in the standard-data memory 34.

Figure 14:
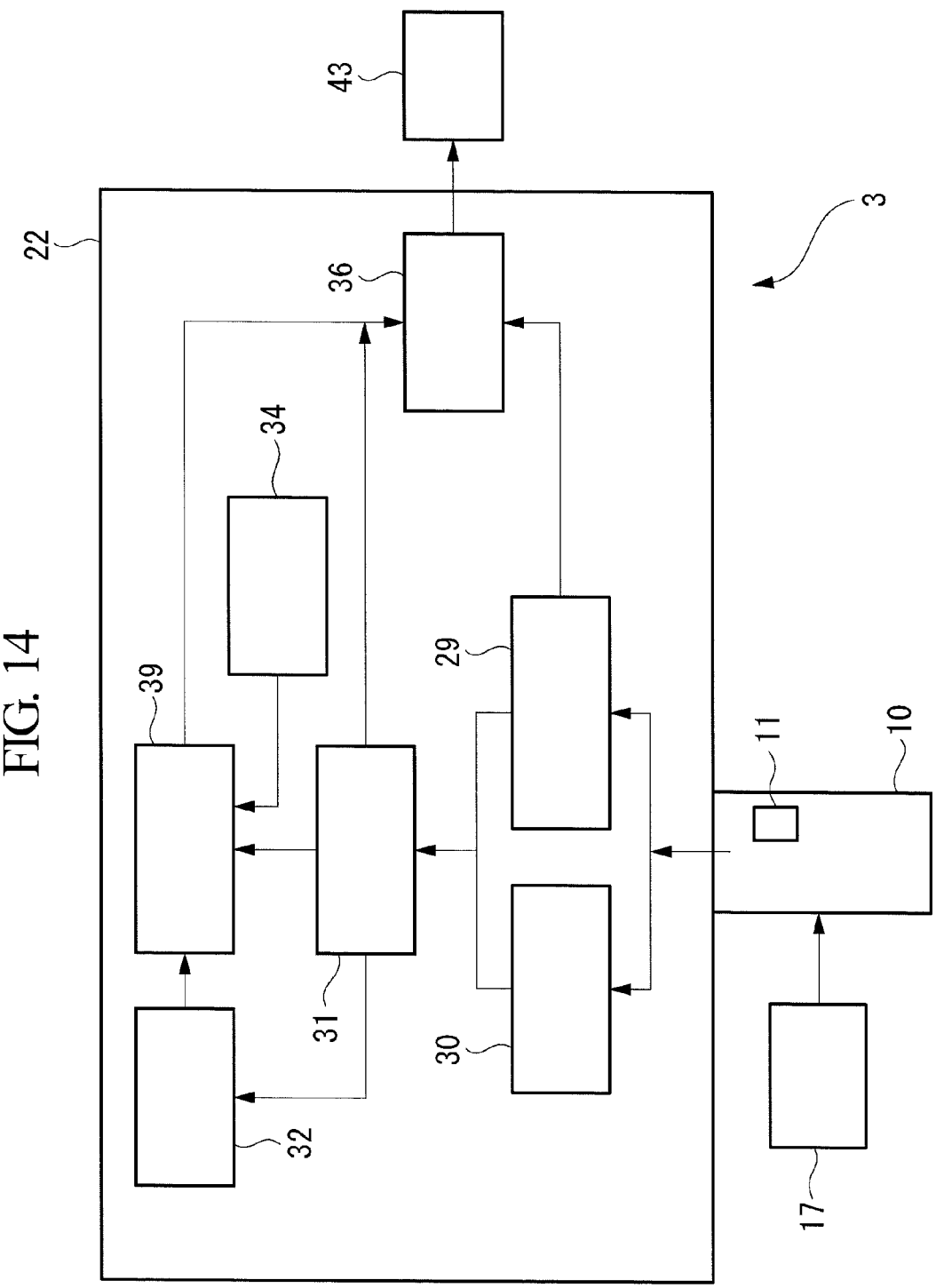
FIG. 14 is a functional block diagram of a fluorescence observation device according to a third embodiment of the present invention.

As shown in FIG. 14, in the fluorescence observation device 3 according to this embodiment, the image computation unit 22 is provided with, as its functions, the white-light image data acquisition unit 29, the fluorescence image data acquisition unit 30, the quantification computation unit (normalization computation unit) 31, the minimum-value acquisition unit (minimum-value storage unit) 32, a linear-correlation computation unit 39, the standard-data memory (standard-data storage unit) 34, and the image combining unit (state judging unit) 36.

The linear-correlation computation unit 39 performs calculation processing for constants a and c in the following equation (1), which shows the correlative relationship between the lesion level and the gradation value for an examinee, from a minimum value ($1, C_1$) of the normalized fluorescence intensities computed by the quantification computation unit 31 and a maximum value ($5, C_5$) of the standard data stored in the standard-data memory 34.

$$y = a(x-5) + c \quad (1)$$

The linear-correlation computation unit 39 obtains a correlative relationship specific to an individual A, which is a straight line shown in FIG. 17, and, by doing so, it becomes possible to convert the normalized fluorescence intensity data computed by the quantification computation unit 31 to the lesion levels. Then, the lesion level of the observation area is determined from the mathematical equation obtained by the linear-correlation computation unit 39 and the information about the acquired image, and, as with each of the embodiments described above, for example, data indicating the lesion level of 3 or above are superimposed on the white-light image, which is the observation image. In addition, the color display may be used for levels other than level 3.

Figure 18:
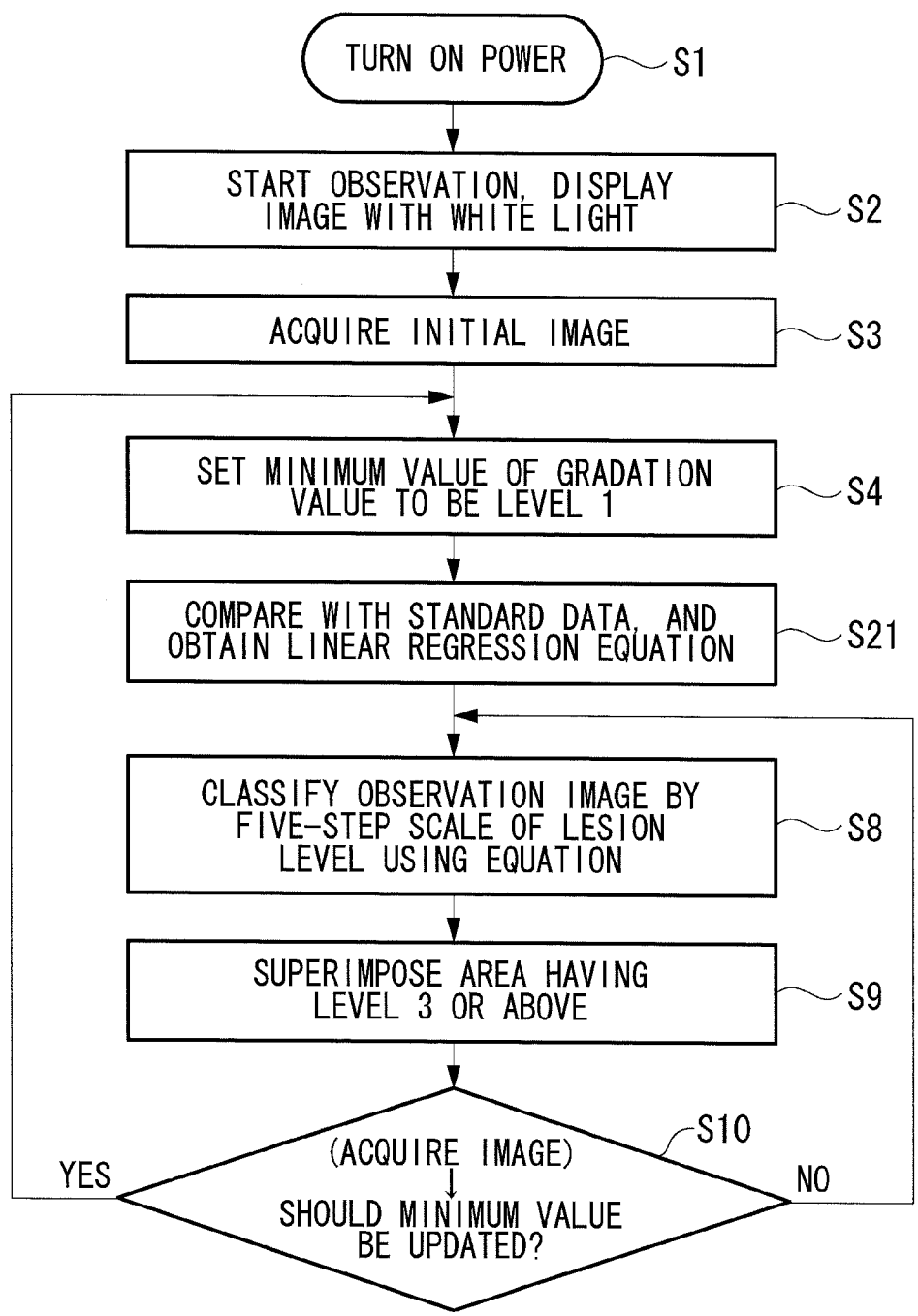
FIG. 18 is a flowchart showing the processing executed by the fluorescence observation device in FIG. 14.

The operation of the fluorescence observation device 3 having the above-described configuration will be described below by using a flowchart shown in FIG. 18.

First, the fluorescence observation device 3 of this embodiment is turned on (Step S1).

Next, once observation of an examination subject is started by inserting the scope 10 into the body cavity, light coming from the light source device 17 is radiated onto the examination subject via the light guide fiber in the scope 10. By doing so, the white-light image data acquisition unit 29 acquires a white-light image generated from the reflected light coming from the examination subject, and the fluorescence image data acquisition unit 30 acquires a fluorescence image generated from the fluorescence emitted from the examination subject (Step S2).

Next, an initial image is acquired from an area assumed to be normal tissue (Step S3). At this time, by dividing the brightness values of the fluorescence image by the brightness values of the white-light image for the individual pixels by means of the quantification computation unit 31, the normalized fluorescence intensities for which the brightness values of the individual pixels have been normalized are computed.

Next, the minimum value is acquired from the normalized fluorescence intensities for the individual pixels, excluding abnormal values, and the acquired minimum value of the normalized fluorescence intensities is set to be the lesion level 1 (Step S4).

Next, the minimum value of the normalized fluorescence intensities for the same image computed by the quantification computation unit 31 and the minimum value of the standard data stored in the standard-data memory 34 are compared, and, by using the equation (1) described above, calculation processing is performed for the constants a and c (Step S21). By applying the normalized fluorescence intensities computed by the quantification computation unit 31 to the mathematical equation calculated in this way, the normalized fluorescence intensities are corrected.

Next, the normalized fluorescence intensities normalized by the image-correction computation unit 35 are classified into levels 1 to 5, that is, the five-step scale of lesion levels, in accordance with the gradation values, and the normalized fluorescence intensities are displayed using the five-step scale (Step S8).

Next, for example, areas at or above level 3 are displayed in color, and, by superimposing them on the white-light image data, the lesion sites are displayed (Step S9). Note that the color display may be used for levels other than level 3.

During the observation, the minimum value of the gradation values is obtained in real time from the image data acquired in the process of inserting the endoscope into the body to update the minimum value of the normalized fluorescence intensities (Step S10). When a normalized fluorescence intensity smaller than an initially-set value is acquired, the process returns to Step S4 to reset the minimum value, and the mathematical equation indicating the correlative relationship between the lesion level and the gradation value is determined on the basis of this value, and the normalized fluorescence intensities are corrected on the basis of this mathematical equation.

Although the fluorescence intensities of a lesion area with a high lesion level are affected little by the individual variation, the influence of individual variation increases in areas closer to the normal area (areas with lower lesion levels). For this point, as described above, with the fluorescence observation device 3 according to this embodiment, states of the examination subject from the minimum value to the maximum value of the standard data are interpolated with the predetermined function, which can then be associated with the individual normalized fluorescence intensities. Accordingly, the states of the examination subject can be judged by eliminating the influence of the individual variation by means of simple computations, which makes it possible to perform the processing involved in judging the state of the examination subject at high speed.

Although the individual embodiments of the present invention have been described in detail as above with reference to the drawings, specific configurations are not limited to these embodiments, and design alterations, etc. within a range that does not depart from the spirit of the present invention are also encompassed.

For example, although the example in which the fluorescence observation device according to the present invention is applied to an endoscope device has been described for each of the embodiments, it may be applied to a microscope device or the like.

Further, although the example in which white light is used as the illumination light has been described for each of the embodiments, it may be reflected light of excitation light or the like, without limitation to white light.

Furthermore, although the white-light image data acquisition unit 29 has been described assuming that it generates a white-light image from reflected light coming from an examination subject, it may generate a return-light image from return light of autofluorescence, etc. from the examination subject.

Moreover, although the lesion levels of the examination subject have been classified by the five-step scale in each of the embodiments, classification by a four-step scale or less or a six-step scale or more may be employed.

REFERENCE SIGNS LIST

1, 2, 3 fluorescence observation device
17 light source device (illumination light source)
20, 21, 22 image computation unit
29 white-light image data acquisition unit (return-light image generation unit)
30 fluorescence image data acquisition unit (fluorescence image generation unit)
31 quantification computation unit (normalization computation unit)
32 minimum-value acquisition unit (minimum-value storage unit)
33 correction-value determining unit (minimum-value updating unit)
34 standard-data memory (standard-data storage unit)
35 image-correction computation unit
36 image combining unit (state judging unit)
38 appropriate-standard-data determining unit
39 linear-correlation computation unit
43 monitor

The invention claimed is:

1. A fluorescence observation device comprising:
   an illumination light source that generates illumination light and excitation light to be radiated onto an examination subject;
   a return-light image generating unit that generates a return-light image by capturing return light coming from the examination subject due to the illumination light emitted from the illumination light source;
   a fluorescence image generating unit that generates a fluorescence image by capturing fluorescence generated at the examination subject due to the excitation light emitted from the illumination light source;
   a normalization computation unit that computes normalized fluorescence intensities, which are brightness values of individual pixels in the fluorescence image generated by the fluorescence image generating unit normalized by brightness values of corresponding pixels in the return light image;
   a standard-data storage unit that stores standard data that indicate a typical correspondence relationship between the normalized fluorescence intensities and states of the examination subject; and
   a state judging unit that judges the states of the examination subject that correspond to the individual normalized fluorescence intensities on the basis of a minimum value of the normalized fluorescence intensities computed by the normalization computation unit and the standard data stored in the standard-data storage unit.

2. A fluorescence observation device according to claim 1, wherein the state judging unit calculates the difference between a minimum value of the normalized fluorescence intensities in the same image computed by the normalization computation unit and a minimum value of the standard data, and judges, by using the standard data, states of the examination subject which correspond to the corrected fluorescence intensities obtained by adding the calculated difference to the individual normalized fluorescence intensities.

3. A fluorescence observation device according to claim 2, further comprising:
   a minimum-value storage unit that stores a minimum value of the normalized fluorescence intensities in the same image computed by the normalization computation unit; and
   a minimum-value updating unit that updates the minimum value stored in the minimum-value storage unit in the case in which a minimum value of the normalized fluorescence intensities in a newly acquired image for the same imaging target is smaller than the minimum value stored in the minimum-value storage unit.

4. A fluorescence observation device according to claim 1, wherein
   the standard-data storage unit stores multiple sets of standard data having different minimum values; and
   the state judging unit selects the standard data having a minimum value closest to the minimum value of the normalized fluorescence intensities in the same image, which are computed by the normalization computation unit, and judges, by using the selected standard data, states of the examination subject which correspond to the individual normalized fluorescence intensities.

5. A fluorescence observation device according to claim 1, wherein the state judging unit interpolates states of the examination subject from the minimum value to the maximum value of the standard data stored in the standard-data storage unit with a predetermined function to be associated with the individual normalized fluorescence intensities between the minimum value of the normalized fluorescence intensities in the same image calculated by the normalization computation unit and the maximum value of the normalized fluorescence intensities in the standard data.

* * * * *